United States Patent
Bob et al.

(10) Patent No.: US 7,914,448 B2
(45) Date of Patent: Mar. 29, 2011

(54) COOLING MEANS FOR ELECTRONIC COMPONENTS PREFERABLY OF AN ENDOSCOPE

(75) Inventors: Konstantin Bob, Weinheim (DE); Fritz Pauker, Kissing (DE); Thomas Viebach, Diepoltshofen (DE)

(73) Assignee: invendo medical, GmbH (DE)

( * ) Notice: Subject to any disclaimer, the term of this patent is extended or adjusted under 35 U.S.C. 154(b) by 1309 days.

(21) Appl. No.: 11/477,002

(22) Filed: Jun. 28, 2006

(65) Prior Publication Data

US 2007/0015962 A1    Jan. 18, 2007

(30) Foreign Application Priority Data

Jul. 1, 2005    (DE) .......................... 10 2005 030 861

(51) Int. Cl.
  *A61B 1/06*    (2006.01)
  *A61B 1/00*    (2006.01)
(52) U.S. Cl. .......................... 600/175; 600/129; 600/172
(58) Field of Classification Search ................... 600/127, 600/129, 136, 141, 160, 172, 175
See application file for complete search history.

(56) References Cited

U.S. PATENT DOCUMENTS

2005/0075538 A1 *    4/2005    Banik et al. .................... 600/141

FOREIGN PATENT DOCUMENTS

JP    02278219 A  *  11/1990
JP    10216085 A  *  8/1998

* cited by examiner

*Primary Examiner* — Thomas J Sweet
*Assistant Examiner* — Ryan Henderson
(74) *Attorney, Agent, or Firm* — Hanley, Flight & Zimmerman, LLC

(57) ABSTRACT

A cooling structure of a heat-generating electronic component including a cooling circuit, which includes a cooling fluid delivery unit, a first heat exchanger for absorbing and discharging thermal energy at the heat-generating electronic component as well as a control structure. The control structure adjusts the cooling fluid flow and thus the cooling capacity of the heat exchanger to such value that at a predetermined temperature in the area of the electronic component a balance is brought about between the heat quantity generated and the heat quantity discharged. The cooling structure is inserted in the deflecting forming a bendable adapter outside the end cap of an endoscope.

13 Claims, 3 Drawing Sheets

COOLING MEANS FOR ELECTRONIC COMPONENTS PREFERABLY OF AN ENDOSCOPE

BACKGROUND OF THE INVENTION

1. Field of the Invention

The present invention relates to a cooling means for heat-generating electronic components, preferably of an endoscope.

2. Discussion of the Prior Art

Electronic parts such as photosensitive sensors, light-emitting diodes (LED) etc. have been increasingly employed in medical apparatuses, for instance in endoscopic instruments. Endoscopes usually have at their distal end a visual means in the form of a photosensitive microchip, an optical means arranged upstream as well as a lighting means. Especially in such instruments it is necessary to compensate the heat caused by the lighting means as well as by the body temperature itself by appropriate cooling means or to protect the photosensitive electronic components against overheating by suitable insulation.

Therefore, from DE 196 26 433 A1 an endoscope head for an endoscope suited for diagnostic and therapeutic purposes in body cavities comprising a lighting means, an optical means as well as an image detecting means has become known which includes light-emitting elements disposed at its distal face and an integrated image forming means behind endoscope optics. Moreover, according to this prior art a cooling means is provided for passing through a cooling fluid, the cooling fluid being passed by the image forming means. In this way it is achieved that the heat-sensitive image detecting means is protected against overheating so as to hereby improve the image quality as a whole.

However, it has turned out that the cooling of the image forming means itself is insufficient as regards the overall function of an endoscope head of this species. As already explained in the beginning, such endoscope heads are equipped with a plurality of electronic and hydraulic/pneumatic means, where appropriate, which must not be exposed to thermodynamic loads or may only be exposed to small thermodynamic loads. In particular the focusing device of the endoscope optics is especially heat-sensitive, because in the case of an increase in temperature an optimum adjustment of the optical elements is no longer possible.

In order to solve this problem, from US 2005/0075538 A1 an endoscope of the one-way type has become known which equally utilizes a cooling means for electronic components, but this cooling means is associated with the LED. In other words, the LED are designed as part of the cooling means which is formed such that it can be fitted into a front cap of the endoscope in which also the other components specific to the endoscope such as optics, spraying means and the like are accommodated.

To this end, the cooling means is in the form of a semi-cylindrical collar into which plug-in connections for the LED are integrated and which shows mounts for receiving the LED at its end face. Moreover, hereby the entire optics including the lens system as well as photosensitive sensor are enclosed by the cooling means and are thus thermally shielded against the LED.

The inventor of the present invention found, however, that this special design of the cooling means further reduces the construction space which is extremely restricted in endoscopes anyway. Moreover the LED according to this prior art are still capable, despite the cooling, of contacting tissue of the body cavity to be examined and possibly of causing even burnings, depending on the alignment.

Therefore, it is the object of the present invention to provide a generic cooling means for electronic components, especially for use in medical instruments, which features a higher efficiency especially also for avoiding damage of tissue.

This object is achieved by a generic cooling means comprising the features according to the enclosed claim 1.

SUMMARY OF THE INVENTION

The core of the invention substantially does not consist, contrary to prior art, in protecting the heat-sensitive components of an electronic means against heat load but in destroying heat energy at the locations where heat is generated. It is crucial in this context that the cooling means is arranged with respect to the electric components to be cooled in a direction in which especially in the case of endoscopes there is still sufficient construction space available, i.e. seen in the direction of the endoscope behind the heat-generating electric components or on the back of the printed circuit board supporting the heat-generating electric components.

According to the invention, it is therefore provided, in the case of mounting in an endoscope, to accommodate the optics inherent to the endoscope, lighting means such as LED etc. in the cap forming the endoscope tip, whereas the cooling means is arranged, structurally separated from the cap, in the upstream deflecting, as it is called, i.e. the bendable part of the endoscope shaft.

The lighting means are soldered in a conventional manner onto a printed circuit board forming the lower end of the endoscope cap and preferably including a contacting surface at its lower side. Moreover, the soldering pinches of the lighting means and/or additional contacting pins preferably project from the lower side of the printed circuit board.

The cooling means preferably forms the outermost end face of the deflecting and has a heat-conducting cover on the lower side of which a first heat exchanger is provided and which can be brought into thermal contact with the printed circuit board when mounting the endoscope.

Furthermore, the cooling means according to the invention provides a cooling circuit consisting of a cooling fluid pump, the first heat exchanger for absorbing and discharging thermal energy at a heat-generating electronic component, a second heat exchanger for discharging the thermal energy absorbed to the atmosphere as well as a control means consisting of a thermal energy detecting unit for detecting the heat quantity discharged by the heat-generating electronic component as well as an adjusting unit for adjusting a fluid flow in response to the detected thermal energy in such manner that in the event of a predetermined temperature a balance is adjusted between the generated heat quantity and the discharged heat quantity.

Ultimately it is provided according to the invention to insert each of the lighting means, preferably LED, accommodated in the cap of the endoscope into a reflector in the shape of a goblet having a preferably parabolic longitudinal section, the reflector bridging the distance between the printed circuit board forming the back plate of the cap, on which the lighting means are arranged, and the front side of the cap.

Further advantageous configurations of the invention are the subject matter of the other subclaims.

BRIEF DESCRIPTION OF THE DRAWINGS

Hereinafter the invention will be illustrated in detail by way of preferred embodiments with reference to the accompanying Figures.

DETAILED DESCRIPTION OF THE PREFERRED EMBODIMENTS

Figure 1:
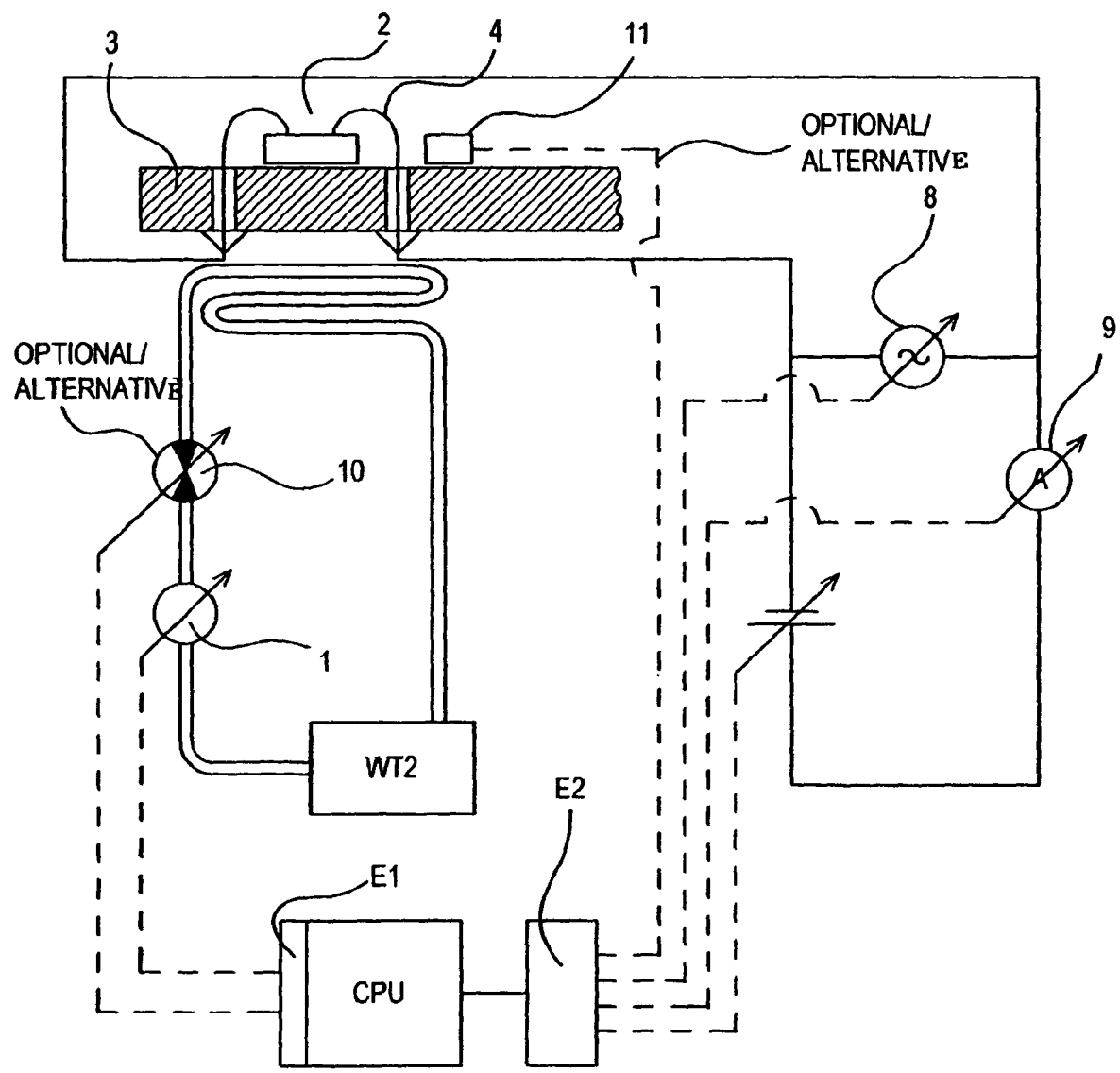
FIG. 1 shows a basic representation of a cooling means according to the invention in accordance with a first preferred embodiment of the invention.

According to the basic representation in FIG. 1, the cooling means according to the invention comprises a cooling circuit for cooling a heat-generating electronic component for instance of a lighting means, preferably LED, as well as a control means for adjusting the fluid flow as a function of the currently generated heat quantity. As an alternative hereto it is also possible, of course, to determine the generated heat quantity in advance for the specific component and corresponding to the operating conditions to be expected and to pre-adjust the discharge rate (supply rate) of cooling fluid in accordance with the estimated, presumed generated heat quantity.

The cooling circuit according to the invention comprises a feed pump 1, a first heat exchanger WT1 which is fluid-connected through a feed passage to the feed pump 1 as well as a second heat exchanger WT2 which is fluid-connected to the first heat exchanger WT1 and to the feed pump 1 (closed circuit). As an alternative hereto, it is also possible to omit the second heat exchanger WT2 and, instead, to directly discharge the used, i.e. heated cooling fluid (open circuit).

As one can further take from the basic diagram according to FIG. 1, the first heat exchanger WT1 is provided directly in the area of a heat-generating electric component 2, for instance a lighting means such as a LED or a power transistor which is soldered/plugged onto an electric printed circuit board (PCB) 3.

Tests have demonstrated that up to 80% of the thermal energy generated by an electronic component 2 such as an LED is transmitted via the electric connecting pinches 4 preferably to the printed circuit board 3. For this reason, it turns out to be especially efficient to locate the heat exchanger WT1 below the printed circuit board 3 in the area of the soldering points of the conducting pinches 4 of the heat-generating electric component 2.

Figure 3:
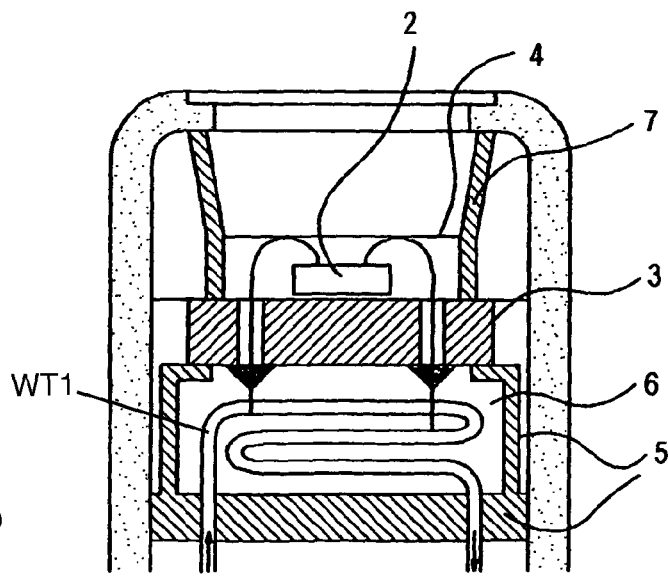
FIG. 3 shows a basic side view of the electronic printed circuit board and the cooling means according to FIG. 2.

In FIG. 3 a basic arrangement of the heat exchanger WT1 below a heat-generating electric component 2 is represented.

In accordance with FIG. 3 the printed circuit board 3 is supported on a base member 5 which forms a cooling chamber 6 below the printed circuit board 3.

As it is furthermore represented enlarged in FIG. 3, the connecting pinches 4 of the electric component 2 project in portions into the cooling chamber 6 so as to discharge heat to the heat exchanger WT1 passed through the cooling chamber 6. The heat exchanger WT1 is represented as cooling coil in a closed structure in FIG. 3. However, it is also possible to seal the cooling chamber 6 by the printed circuit board 2 itself or by a heat transfer plate to be brought into contact with the printed circuit board and to introduce the cooling fluid directly into the cooling chamber 6 in an open structure.

According to FIG. 3, the electric component 2 is in the form of a lighting means, preferably LED, which is surrounded by a reflector 7, preferably made of aluminum, in funnel shape so as to increase the light efficiency. As is known, aluminum is an excellent heat conductor.

Since, as explained in the foregoing already, at least 20% of the total heat quantity generated is still transmitted via the electric component 2 itself to the environment, it is certainly possible that the reflector 7 is heated. For this reason it is optionally possible to guide the heat exchanger WT1 in addition at least in portions around the reflector 7 so as to discharge the heat quantity absorbed there via the cooling fluid passed through.

The present cooling means for electronic components is preferably used in medical instruments, such as especially endoscopes. Endoscopes are usually equipped with endoscope heads in which a plurality of electric, optical as well as hydraulic parts are disposed closely packed and, as a consequence, mutually influence each other mechanically as well as thermodynamically. Most recently endoscopes have been provided with photosensitive microchips upstream of which an optical means is provided so as to transmit visual image signals via a line system to a computer. Photosensitive microchips of this type and the optical means arranged upstream thereof are extremely heat-sensitive and, therefore, have to be protected against overheating especially when used inside a body cavity.

In order to obtain optimum image signals an additional lighting means in the form of the afore-described LED is necessary which, despite a high light efficiency, still generates a considerable thermal energy. Furthermore, the supply of the endoscope head with electric energy and/or a hydraulic/pneumatic fluid basically represents a problem because of the narrow space. For instance, the diameters of supply and discharge passages cannot be designed to have any size but they have to be adapted to the space available without compromise.

For this reason, it is provided according to the invention to detect the heat quantity generated by an electric component 2, such as the LED, and to adapt the quantity of cooling fluid required for cooling the heat-generating electric component 2 to the detected heat quantity. In this way, an optimum efficiency of the entire means can be achieved and the energy consumption of the pump 1 and the cross-section of the fluid passages of the cooling circuit, respectively, can be optimized.

In accordance with FIG. 1 it is provided for this purpose to assign an electric measuring circuit, which consists of a voltmeter 8 and a current meter 9 whose currently detected values are supplied to a computing unit (CPU), to the heat-generating electric component 2.

In the CPU, value tables specific to the component with respect to voltage, current and thermal energy are stored. Such tables can be drafted in advance by analysis for each specific component. In other words, electric components generate in the case of particular current-voltage ratios a predetermined thermal energy which can be detected by tables. The CPU compares the thermal energy obtained from the measured current/voltage values to the current discharge rate of cooling fluid through the pump 1 and appropriately controls the latter.

In other words, for a predetermined passage cross-section and heat exchanger specific heat quantities can be determined by analysis which can be maximally discharged in the case of a predetermined capacity of the pump 1. Therefore the CPU controls the pump 1 such that the capacity thereof and the quantity of cooling fluid pumped by the same are just sufficient to absorb the calculated heat quantity generated by the respective electronic component.

As an alternative or option it is also possible, of course, to arrange a controllable throttle valve 10 instead of and/or in addition to the controllable pump 1 downstream of the pump 1 so as to control the capacity of cooling fluid in response to the calculated thermal energy. It is also possible to reduce the electric energy supplied to the electronic component 2 when exceeding predetermined thermal energy generated, especially in case that the maximum cooling capacity of the cooling means becomes insufficient.

As further shown in FIG. 1, in addition or as an alternative to the illustrated electric control circuit a heat sensor 11 may be provided which is arranged in direct vicinity of the heat-generating electric component 2 and enters the current temperature values into the CPU. The controllable pump 1 and/or the control valve 10 arranged downstream thereof is/are appropriately controlled by a control unit E1 of the CPU.

Figure 2:
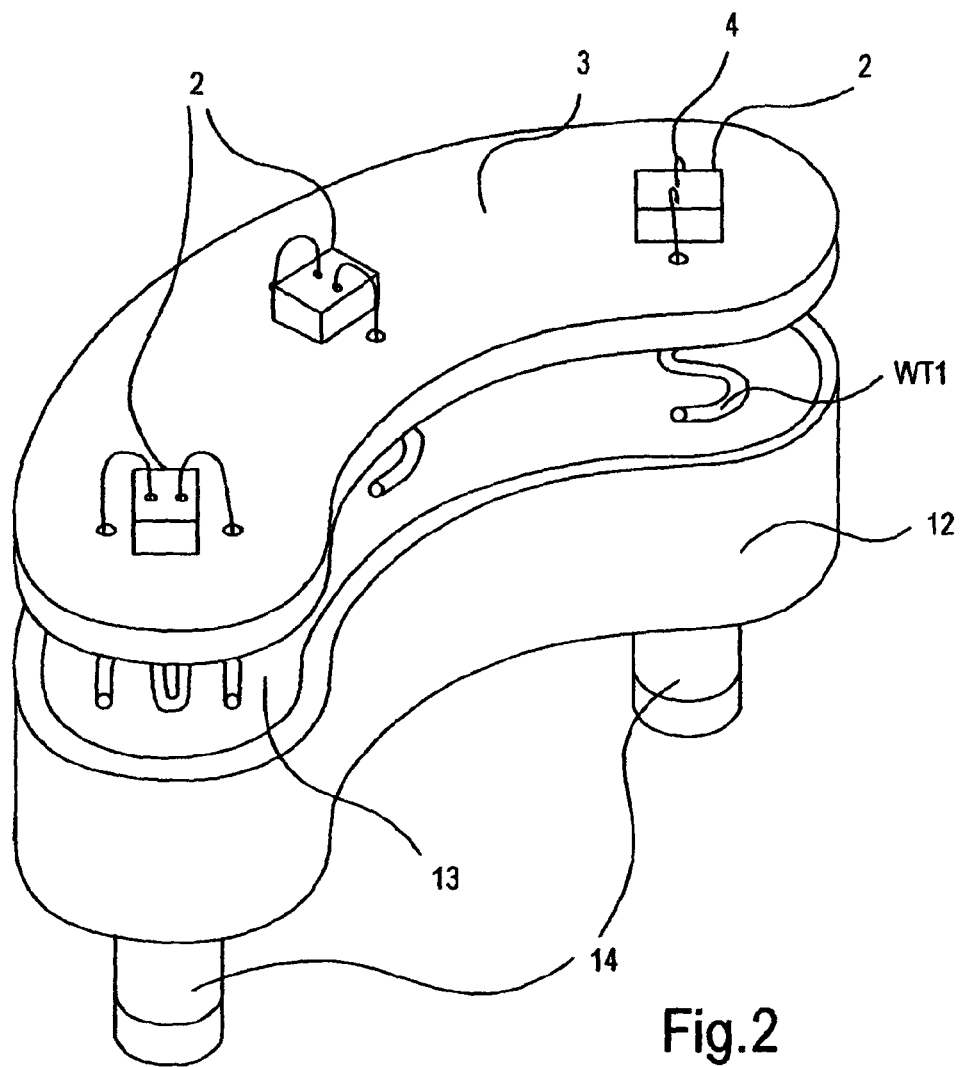
FIG. 2 shows a basic representation of an electronic printed circuit board as part of the cooling means according to the invention in accordance with FIG. 1.

In FIG. 2 a first example of a structural design of the cooling means according to the invention, especially in the area of the printed circuit board 3 and the first heat exchanger WT1, is shown. This means is preferably used in the area of the distal end portion of an endoscope not shown in more detail.

According to FIG. 2, the printed circuit board 3 represented there consequently has a divided circle shape and in the present case supports three light-emitting diodes (LED). The printed circuit board 3 is glued onto a base element 12 the outer shape of which is adapted to the shape of the printed circuit board 3, i.e. it is equally in the form of a divided circle.

The base element 12 forms a trough-shaped recess 13 which is closed at the upper side of the base element 12 by the printed circuit board 3 when the latter is glued thereon. Inside the trough-shaped recess 13 the heat exchanger WT1, represented by three heat coils according to FIG. 2, is accommodated. Finally two connecting elements (screws, stubs, etc.) 14 arranged at the end side via which the printed circuit board 3 is supplied with electric energy and the heat exchanger WT1 is supplied with cooling fluid are provided at the lower side of the base element 12 opposed to the printed circuit board 3.

It is finally outlined that, in terms of function, the base element 12 according to FIG. 2 corresponds to the base 5 according to FIG. 3. Therefore it is basically possible to design the trough-shaped recess 13 to be sealing and to directly flood it with cooling fluid. When mounted in an endoscope, the base element 12 including the lighting means/printed circuit board fixed thereto is arranged preferably in the deflecting below the cap forming the endoscope tip, wherein the reflector 7 shown in FIG. 3 bridges the distance between the lighting member and the light emergent edge at the front of the cap which is not shown in more detail.

It is ensured by this measure that the restricted space inside the cap for receiving optical means, fluid passages, spraying means etc. is no more narrowed, on the other hand it is prevented hereby that the lighting means comes too close to the ambient tissue of the body cavity to be examined or even contacts the tissue thus causing burns.

Figure 4:
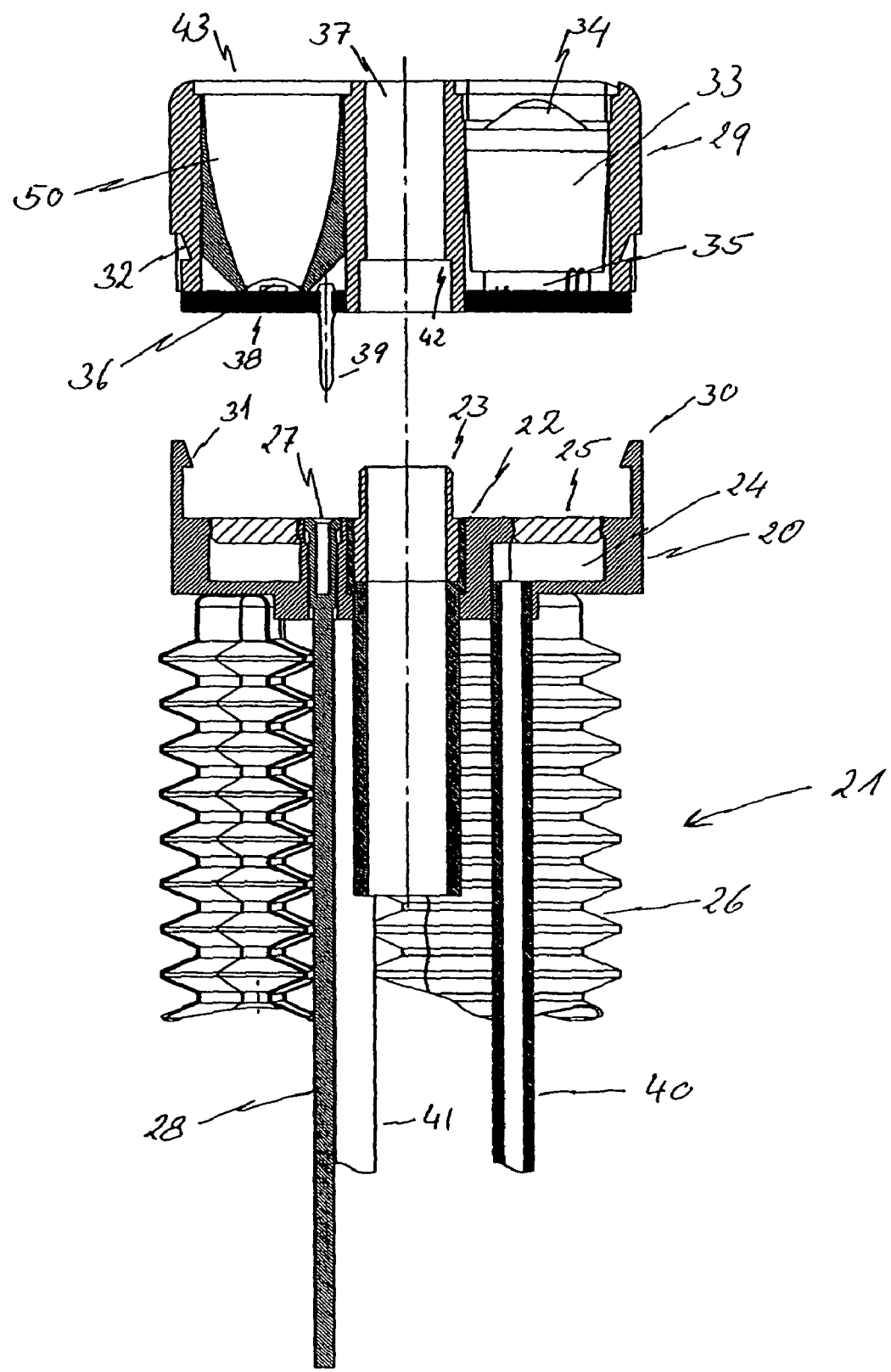
FIG. 4 shows the distal end portion of an endoscope comprising a cooling means in accordance with a second preferred embodiment of the invention.

In FIG. 4 a second preferred embodiment of the invention is shown.

Accordingly, the cooling means forms the end plate 20 of a bendable adapter 21 of the shaft of an endoscope (hereinafter referred to as deflecting) which has a cup or bowl shape. The cup 20 has a central through-bore 22 into which a pipe-shaped or nozzle-shaped projection 23 of the cup is inserted. Hereby an annular groove is formed which constitutes a cooling chamber 24 of the cooling means.

The open front of the cup-shaped end plate 20 is covered by an annular disk or cover plate 25 consisting of thermally conductive material. The lower side of the end plate 20 forms a stop face for actuating elements 26 of the deflecting such as hydraulically/pneumatically activated bellows, piezo elements, traction/pressure cables and the like, as they are known already from prior art. Moreover, a number of electric plug-in connections 27 connected to a control unit (not shown in detail) via electric cables 28 are formed in the end plate 20.

The end plate 20 furthermore forms at its outer front a terminal for an end cap 29 of the endoscope. In the present case, this terminal consists of a number of locking elements (clips) in the form of lugs or brackets 30 arranged at the edge of the end plate 20 and extending axially therefrom. Each bracket 30 includes at its end side a stop catch 31 which is adapted to be engaged by locking with a corresponding cap-side undercut 32.

In the end cap 29 a plurality of components is provided, such as for instance an optical means 33 consisting of a lens system 34 and a photosensitive sensor 35, lighting means 36, preferably LED, a central through-passage for passing medical instruments therethrough etc.

As it is illustrated in FIG. 4, at least the lighting means 36 are arranged on a printed circuit board 38 forming a lower cover of the end cap 29. A number of connecting pins 39 which, when mounting the cap 29 on the end plate 20 of the deflecting, are pressed into the electric plug-in connections 27 (sockets) of the latter project from the lower side of the printed circuit board 38. For a true-to-size mounting of the end cap 29 the central nozzle-shaped projection 23 of the cup-shaped end plate axially projects from the heat conducting cover plate 25 for being adapted to be fitted into the working passage 37 of the end cap 29 as a centering aid. The end cap 29 is placed at its lower front especially above the lower-side printed circuit board 38 onto the end plate 20 of the deflecting and is fixed, in addition to the holding force of the locking elements 30, for instance by gluing. In the mounting position the heat conducting cover plate 25 is adjacent to the lower side of the printed circuit board 38 supporting the lighting means such that a heat transfer can take place between the printed circuit board 38 and the end plate.

In accordance with FIG. 4 at least two further fluid passages 40, 41, the one 40 of which forms a supply passage fluid-connected to the cooling chamber and the other 41 forms a discharge passage, are guided through the deflecting.

As an alternative to the above-described design, it is also possible in the second embodiment according to FIG. 4 to dispense with the cover plate 25 and instead to have the printed circuit board 38 itself directly cover the cooling chamber 24 in an open design when the cap 29 is mounted on the end plate 20. In this latter case an annular seal (not shown in more detail) could be provided at the front circumferential surface of the end plate 20 as well as at the front side of the central projection 23 of the cup-shaped end plate 20, wherein, when mounting the end cap 29 on the deflecting 21, the annular seal contacts the front side of the end cap 29 and a corrugated shoulder 42 of the central working passage 37 of the cap 29 and thus radially seals the cooling chamber 24.

Ultimately, in FIG. 4 a reflector 50 is illustrated as a subject matter of the invention to be considered separately.

As explained already in the foregoing, by axially withdrawing the lighting means 36 and by moving the cooling means from the end cap 29 into the deflecting 21 disposed directly therebehind it is obtained that inside the end cap 29 of the endoscope sufficient space remains for the other necessary components. Moreover, a direct contact of the lighting means 36 with ambient tissue is prevented. In order to nevertheless ensure sufficient lighting of the environment, between the lighting means 36 preferably in the form of a LED and the foremost light emerging edge which is closed by a pane/ window 43 in the cap 29 the reflector 50 is disposed in the form of a goblet preferably parabolic in the longitudinal section. Said goblet is further preferably fixed on the printed circuit board 38 and, upon mounting the printed circuit board 38 on the cap 29, is inserted into the latter.

The goblet-shaped reflector 50 can consist of a plastic material silvered on the inside or of aluminum (polished and/or silvered). As an alternative, it is also possible to use, instead of the reflector 50, a light conductor in the form of a glass body or a different body of photoconductive material which is preferably silvered at its circumferential surface.

The invention claimed is:

1. An endoscope comprising:
   an end cap accommodating at least a lighting means mounted on an electric circuit board and an optical means comprising a lens system and a light sensitive sensor, wherein the circuit board forms an axially lower sealing cover of the end cap, the end cap being mounted on the front of a manually bendable adapter of an endoscope shaft; and
   a cooling means for cooling electronic components including the lighting means inside the end cap, wherein the cooling means comprises:
      a cooling circuit feeding a cooling fluid; and
      a cooling chamber,
   wherein the cooling circuit and the cooling chamber form part of the bendable adapter and wherein the cooling circuit and the cooling chamber are axially distanced from the end cap,
   wherein an axially upper sealing cover of the cooling chamber is formed by at least one of the electric circuit board or an axially upper end plate that abuts the electric circuit board, and
   wherein the cooling chamber is fluid-sealed by the electric circuit board or by the axially upper end plate so that the cooling fluid is feedable through the cooling chamber so that upon placing the end cap onto the adapter, the cooling means is brought into thermal contact directly with the electronic components to be cooled or with bridging parts connected to the electronic components.

2. An endoscope according to claim 1, wherein the cooling means forms the end plate of the bendable adapter, and a heat exchanger is accommodated in the cooling chamber.

3. An endoscope according to claim 2, wherein a lower side of the circuit board constitutes an abutting surface that is engageable with the end plate of the bendable adapter.

4. An endoscope according to claim 2, wherein the end plate is cup-shaped having a central pipe-shaped projection, wherein an annular groove is formed that is closed at a front side of the end plate by a cover plate made of heat conducting material.

5. An endoscope according to claim 1, wherein a reflector that is goblet-shaped in longitudinal section and is made of glass or transparent plastic material is provided for bridging the distance between the lighting means and a light emerging opening at a front side of the end cap.

6. An endoscope according to claim 1, wherein the cooling chamber is flooded with a cooling fluid delivered via feed and discharge pipes inside the bendable adapter.

7. An endoscope according to claim 6, wherein a lower side of the circuit board constitutes an abutting surface that is engageable with the end plate of the bendable adapter.

8. An endoscope according to claim 6, wherein the end plate is cup-shaped having a central pipe-shaped projection, wherein an annular groove is formed that is closed at a front side of the end plate by a cover plate made of heat conducting material.

9. An endoscope according to claim 1, wherein a light conductor made of glass or transparent plastic material is provided for bridging the distance between the lighting means and a light emerging opening at a front side of the end cap.

10. An endoscope as defined in claim 1, wherein the cooling circuit comprises a feed pump.

11. An endoscope as defined in claim 1, wherein the end plate comprises at least one axially extending bracket that is configured to interlock with the end cap.

12. An endoscope as defined in claim 11, wherein the bracket comprises a catch stop to engage an undercut on the end cap.

13. An endoscope as defined in claim 1, wherein the cooling circuit includes a longitudinally extending fluid supply passage and a longitudinally extending fluid discharge passage.

* * * * *